United States Patent
Yanagihara et al.

(10) Patent No.: US 10,201,394 B2
(45) Date of Patent: Feb. 12, 2019

(54) MEDICAL MANIPULATOR SYSTEM

(71) Applicant: OLYMPUS CORPORATION, Tokyo (JP)

(72) Inventors: Masaru Yanagihara, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/804,068

(22) Filed: Nov. 6, 2017

(65) Prior Publication Data
US 2018/0055588 A1 Mar. 1, 2018

Related U.S. Application Data

(63) Continuation of application No. PCT/JP2015/082118, filed on Nov. 16, 2015.
(Continued)

(51) Int. Cl.
*A61B 34/30* (2016.01)
*A61B 34/35* (2016.01)
(Continued)

(52) U.S. Cl.
CPC ........ *A61B 46/10* (2016.02); *A61B 17/00234* (2013.01); *A61B 17/29* (2013.01);
(Continued)

(58) Field of Classification Search
CPC ........ A61B 17/062; A61B 34/37; A61B 1/041
See application file for complete search history.

(56) References Cited

U.S. PATENT DOCUMENTS 5,386,816 A 2/1995 Inoue et al.
6,331,181 B1 12/2001 Tierney et al.
(Continued)

FOREIGN PATENT DOCUMENTS

CN 101416867 A 4/2009
EP 2324789 A1 5/2011
(Continued)

OTHER PUBLICATIONS

Office Action dated Jan. 30, 2018 received in U.S. Appl. No. 15/375,374.
(Continued)

*Primary Examiner* — Bickey Dhakal
*Assistant Examiner* — Charles S Laughlin
(74) *Attorney, Agent, or Firm* — Scully, Scott, Murphy & Presser, P.C.

(57) ABSTRACT

In order to improve work efficiency of inserting manipulators into proximal ends of an over tube, a medical manipulator system includes: manipulators having, at the proximal ends, proximal-end driving parts; an over tube having channels through which the manipulators pass; and a base provided with support parts to which proximal end parts of the over tube are attached, and driving sources that supply driving force to the proximal-end driving parts, wherein each support part includes a movable part movable between a first position where the longitudinal axis of the proximal end part is supported horizontally and a second position where the proximal end is supported at a further position from the top surface, and an urging part that moves the movable part to the second position during the proximal-end driving part is not connected to the driving source.

17 Claims, 9 Drawing Sheets

Related U.S. Application Data

(60) Provisional application No. 62/168,987, filed on Jun. 1, 2015.

(51) Int. Cl.

| | | |
|---|---|---|
| *A61B 46/10* | (2016.01) | |
| *A61B 34/32* | (2016.01) | |
| *A61B 34/37* | (2016.01) | |
| *A61B 34/00* | (2016.01) | |
| *A61B 90/00* | (2016.01) | |
| *A61B 17/29* | (2006.01) | |
| *B25J 3/00* | (2006.01) | |
| *B25J 13/02* | (2006.01) | |
| *A61B 18/14* | (2006.01) | |
| *A61B 90/50* | (2016.01) | |
| *A61B 17/00* | (2006.01) | |
| *A61B 17/34* | (2006.01) | |
| *B32B 3/26* | (2006.01) | |
| *A61B 18/00* | (2006.01) | |

(52) U.S. Cl.
CPC ...... *A61B 17/3423* (2013.01); *A61B 18/1492* (2013.01); *A61B 34/30* (2016.02); *A61B 34/32* (2016.02); *A61B 34/37* (2016.02); *A61B 34/70* (2016.02); *A61B 34/71* (2016.02); *A61B 34/74* (2016.02); *A61B 90/03* (2016.02); *A61B 90/06* (2016.02); *A61B 90/50* (2016.02); *B25J 3/00* (2013.01); *B25J 13/02* (2013.01); *A61B 18/1482* (2013.01); *A61B 2017/00314* (2013.01); *A61B 2017/00323* (2013.01); *A61B 2017/00477* (2013.01); *A61B 2017/00929* (2013.01); *A61B 2018/00077* (2013.01); *A61B 2018/00083* (2013.01); *A61B 2018/1412* (2013.01); *A61B 2034/301* (2016.02); *A61B 2034/302* (2016.02); *A61B 2034/306* (2016.02); *A61B 2090/034* (2016.02); *B32B 3/266* (2013.01)

(56) References Cited

U.S. PATENT DOCUMENTS

| | | | |
|---|---|---|---|
| 7,972,298 B2 | 7/2011 | Wallace et al. | |
| 8,638,057 B2 | 1/2014 | Goldberg et al. | |
| 8,720,448 B2 | 5/2014 | Reis et al. | |
| 2002/0128649 A1 | 9/2002 | Bacher et al. | |
| 2004/0019352 A1 | 1/2004 | Kidooka | |
| 2005/0075739 A1 | 4/2005 | Nishizawa | |
| 2005/0096502 A1 | 5/2005 | Khalili | |
| 2005/0154439 A1 | 7/2005 | Gunderson | |
| 2005/0222495 A1 | 10/2005 | Okada et al. | |
| 2005/0272975 A1 | 12/2005 | McWeeney et al. | |
| 2006/0282063 A1 | 12/2006 | Gotani | |
| 2007/0163597 A1 | 7/2007 | Mikkaichi et al. | |
| 2008/0108443 A1 | 5/2008 | Jinno et al. | |
| 2008/0193260 A1 | 8/2008 | Yokokohji et al. | |
| 2008/0281155 A1 | 11/2008 | Fujikura | |
| 2008/0294004 A1 | 11/2008 | Fujikura | |
| 2009/0018390 A1 | 1/2009 | Honda et al. | |
| 2009/0105726 A1 | 4/2009 | Sugiyama | |
| 2009/0182200 A1 | 7/2009 | Golden et al. | |
| 2009/0248039 A1 | 10/2009 | Cooper et al. | |
| 2009/0275798 A1 | 11/2009 | Naito | |
| 2010/0030023 A1* | 2/2010 | Yoshie | A61B 1/00147 600/117 |
| 2010/0170519 A1 | 7/2010 | Romo et al. | |
| 2010/0298646 A1 | 11/2010 | Stellon et al. | |
| 2010/0318100 A1 | 12/2010 | Okamoto et al. | |
| 2010/0331856 A1 | 12/2010 | Carlson et al. | |
| 2011/0168189 A1 | 7/2011 | Cooper et al. | |
| 2012/0271102 A1 | 10/2012 | Katayama | |
| 2012/0289973 A1 | 11/2012 | Prisco et al. | |
| 2013/0331857 A9 | 12/2013 | Prisco et al. | |
| 2014/0166023 A1* | 6/2014 | Kishi | A61B 17/29 128/849 |
| 2014/0296771 A1* | 10/2014 | Naito | F16C 1/06 604/19 |
| 2015/0238180 A1 | 8/2015 | Weitzner et al. | |

FOREIGN PATENT DOCUMENTS

| | | | | |
|---|---|---|---|---|
| JP | S6272091 U | 5/1987 | | |
| JP | H05095893 A | 4/1993 | | |
| JP | H07095953 A | 4/1995 | | |
| JP | H10276965 A | 10/1998 | | |
| JP | 2004344180 A | 12/2004 | | |
| JP | 2005103741 A | 4/2005 | | |
| JP | 2005287963 A | 10/2005 | | |
| JP | 2006334695 A | 12/2006 | | |
| JP | 2007167644 A | 7/2007 | | |
| JP | 2007517597 A | 7/2007 | | |
| JP | 2007307289 A | 11/2007 | | |
| JP | 2007530155 A | 11/2007 | | |
| JP | 2008114339 A | 5/2008 | | |
| JP | 2008278968 A | 11/2008 | | |
| JP | 2009011809 A | 1/2009 | | |
| JP | 2009100873 A | 5/2009 | | |
| JP | 2009523032 A | 6/2009 | | |
| JP | 2009240657 A | 10/2009 | | |
| JP | 2009268592 A | 11/2009 | | |
| JP | 4420593 B2 | 2/2010 | | |
| JP | 2010035768 A | 2/2010 | | |
| JP | 2010525838 A | 7/2010 | | |
| JP | 2011509718 A | 3/2011 | | |
| JP | 2011072570 A | 4/2011 | | |
| JP | 2011072574 A | 4/2011 | | |
| JP | 2012070953 A | 4/2012 | | |
| JP | 2012152562 A | 8/2012 | | |
| JP | 2013034833 A | 2/2013 | | |
| JP | WO 2013018927 A1 * | 2/2013 | ............ | A61B 17/29 |
| JP | 2014028291 A | 2/2014 | | |
| JP | WO 2014034532 A1 * | 3/2014 | ............... | F16C 1/06 |
| JP | 2014111080 A | 6/2014 | | |
| JP | 2014521375 A | 8/2014 | | |
| JP | 2015006423 A | 1/2015 | | |
| WO | 1997029690 A1 | 8/1997 | | |
| WO | 1998025666 A1 | 6/1998 | | |
| WO | 2005070339 A1 | 8/2005 | | |
| WO | 2005094665 A2 | 10/2005 | | |
| WO | 2007041093 A1 | 4/2007 | | |
| WO | 2007070693 A2 | 6/2007 | | |
| WO | 2009037576 A2 | 3/2009 | | |
| WO | 2009091836 A1 | 7/2009 | | |
| WO | 2010055745 A1 | 5/2010 | | |
| WO | 2012158449 A1 | 11/2012 | | |
| WO | 2013018927 A1 | 2/2013 | | |

OTHER PUBLICATIONS

International Search Report dated Jan. 12, 2016 issued in International Application No. PCT/JP2015/082118.
International Search Report dated Dec. 22, 2015 issued in International Application No. PCT/JP2015/078063.
International Search Report dated Nov. 10, 2015 issued in International Application No. PCT/JP2015/074792.
International Search Report dated Jan. 26, 2016 issued in International Application No. PCT/JP2015/082622.
International Search Report dated Jun. 28, 2016 issued in International Application No. PCT/JP2016/063786.
U.S. Office Action dated Sep. 14, 2017 issued in U.S. Appl. No. 15/375,374.
Office Action dated Jun. 8, 2018 received in U.S. Appl. No. 15/824,481.
Office Action dated Apr. 19, 2018 received in U.S. Appl. No. 15/819,045.

\* cited by examiner

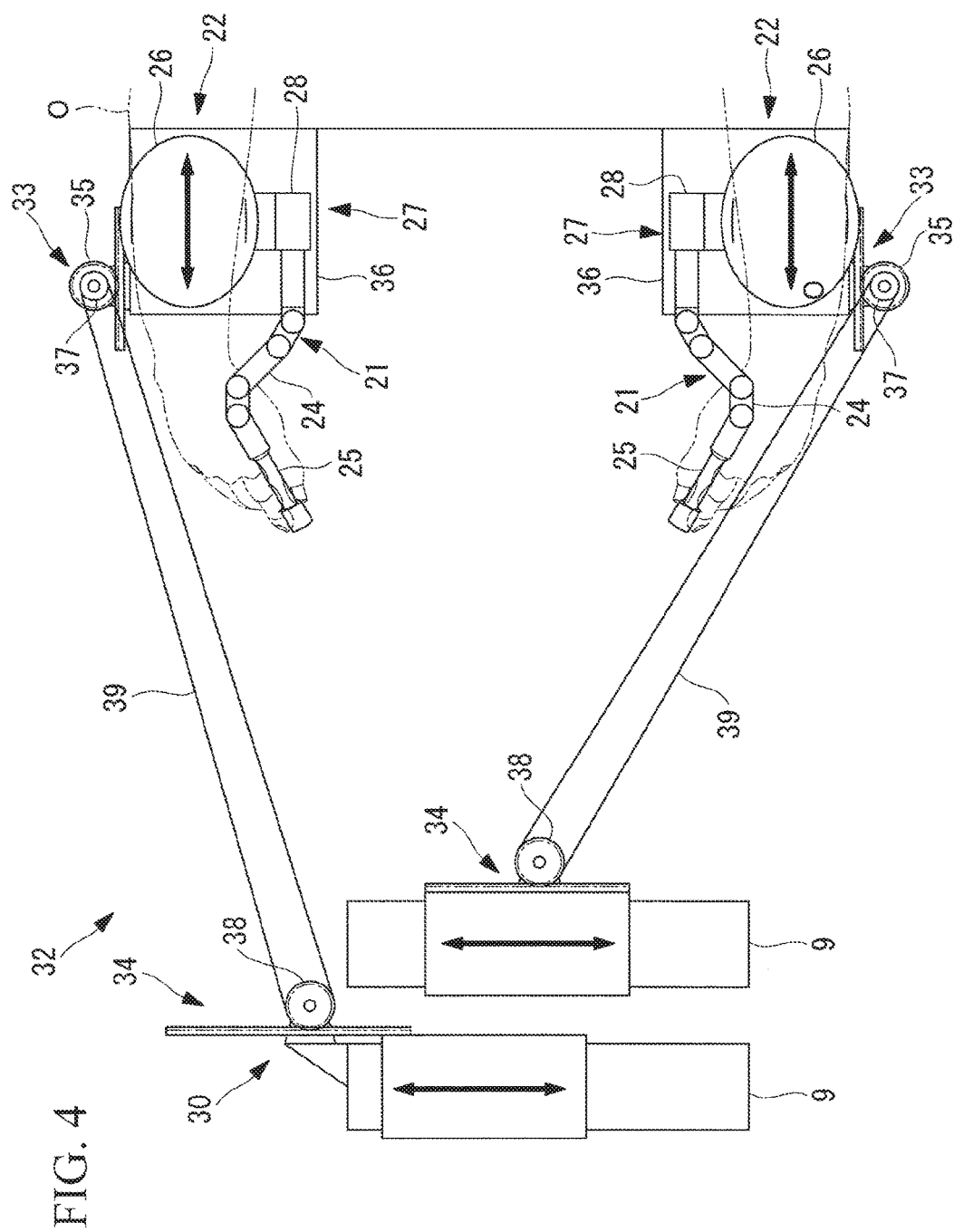

MEDICAL MANIPULATOR SYSTEM

CROSS-REFERENCE TO RELATED APPLICATIONS

This application is a Continuation Application of International Application No. PCT/JP2015/082118 filed on Nov. 16, 2015, which claims priority to Provisional Application No. 62/168,987 filed on Jun. 1, 2015. The contents of International Application No. PCT/JP2015/082118 and Provisional application No. 62/168,987 are incorporated herein by reference in its entirety.

TECHNICAL FIELD

The present invention relates to a medical manipulator systems.

BACKGROUND ART

There is a known two-layer-structure catheter, with an inner catheter inserted through an outer catheter, wherein a connecting part provided on the proximal end side of the outer catheter and a connecting part provided on the proximal end side of the inner catheter are simultaneously attached to or detached from a driving units that are provided side-by-side on a flat base (for example, see PTL 1).

CITATION LIST

Patent Literature

{PTL 1} U.S. Pat. No. 7,972,298

SUMMARY OF INVENTION

An aspect of the present invention is a medical manipulator system to which a manipulator having a treatment part at its distal end section and having a proximal-end driving part for driving the treatment part at its proximal end section is connected, the manipulator system including: a base provided with, on a top surface thereof, a driving source that is detachably connected to the proximal-end driving part of the manipulator when the manipulator is inserted into a channel of the over tube from a proximal end part of the over tube to supply a driving force to the proximal-end driving part, and a support part to which the proximal end part of the over tube is attached, wherein the over tube has the channel through which the manipulator passes in a longitudinal direction of the over tube, wherein the support part includes: a movable part provided so as to be movable between a first position where a longitudinal axis of the proximal end part of the over tube attached to the movable part is supported horizontally and a second position where the proximal end is supported at a position farther from the top surface than at the first position; and an urging part that moves the movable part to the second position during the proximal-end driving part is not connected to the driving source.

BRIEF DESCRIPTION OF DRAWINGS

FIG. 4 is a plan view for explaining second operating parts, instruction transmitting units, and advancing-and-retracting mechanisms of the operation input parts of the medical manipulator system in FIG. 1.

DESCRIPTION OF EMBODIMENTS

A medical manipulator system 1 according to an embodiment of the present invention will be described below with reference to the drawings.

Figure 1:
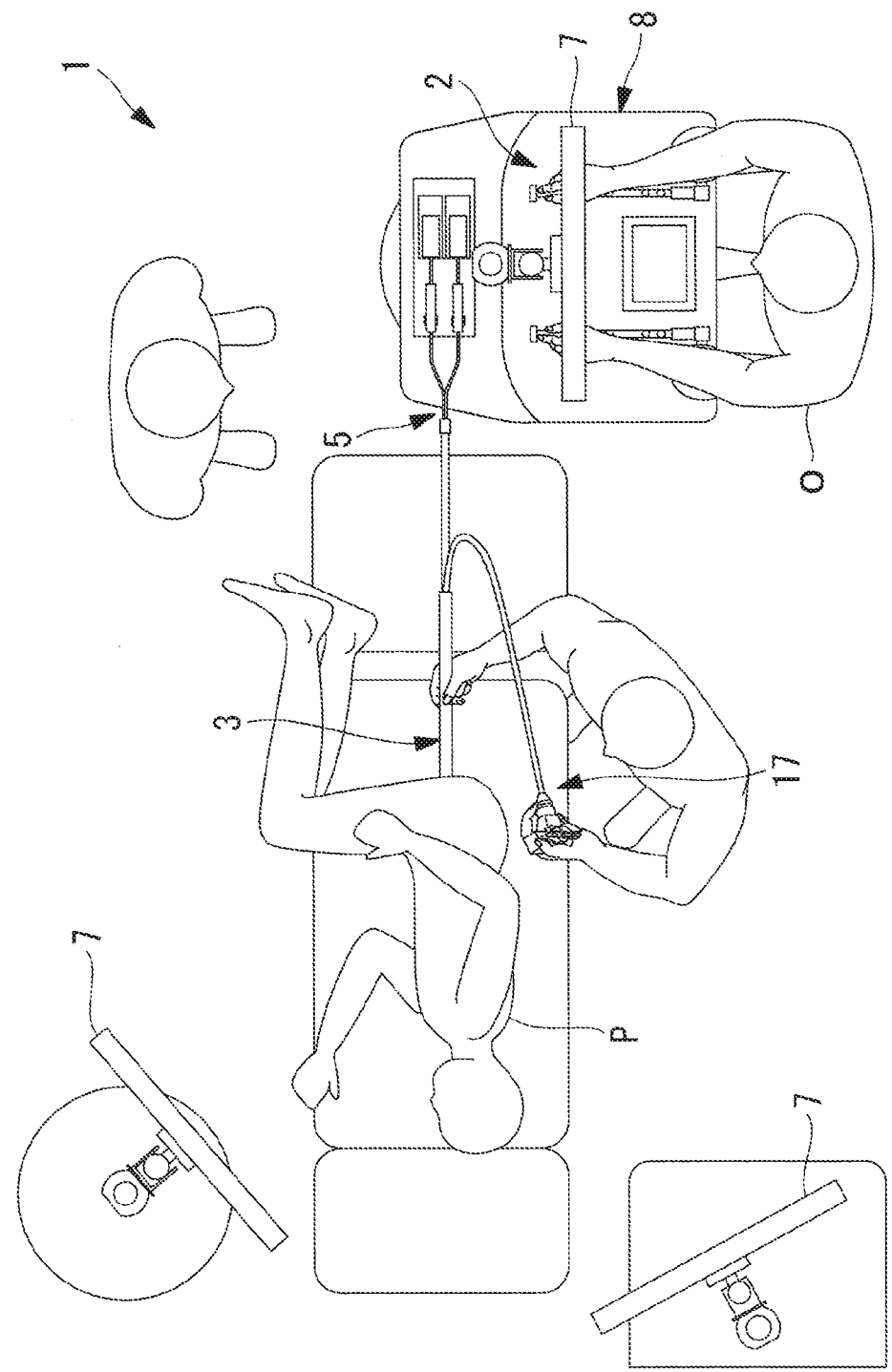
FIG. 1 shows the overall configuration of a medical manipulator system according to an embodiment of the present invention.
Figure 2:
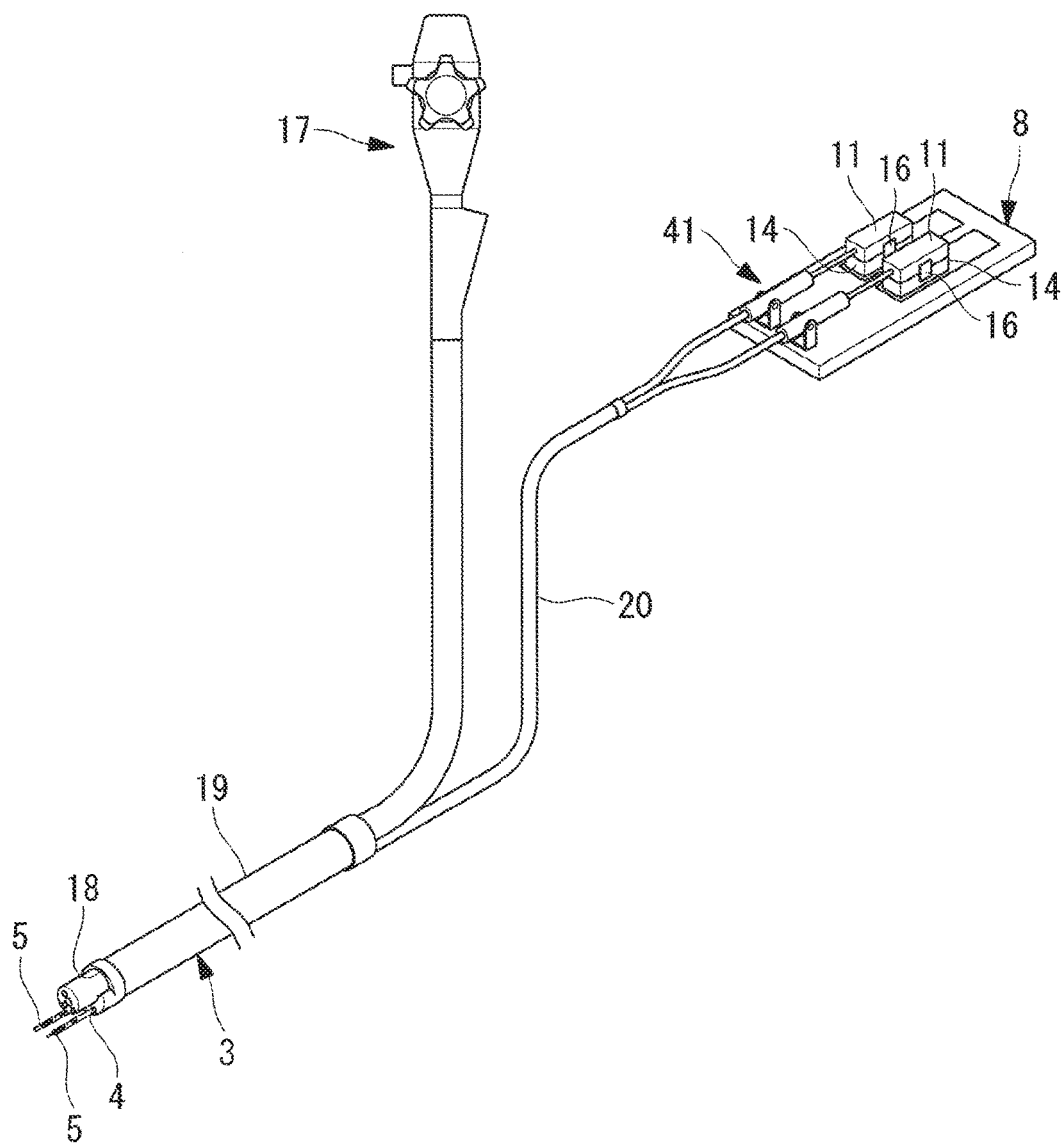
FIG. 2 is a perspective view showing a part of the medical manipulator system in FIG. 1.

As shown in FIGS. 1 and 2, the medical manipulator system 1 according to this embodiment includes: operation input parts 2 that are operated by an operator O; an over tube 3 that is inserted into a body cavity of a patient P; two manipulators 5 that are individually inserted through two channels 4 in the over tube 3; a control unit 6 that controls the manipulators 5 according to the operations of the operation input parts 2; monitors 7; and a console (base) 8 on which the operation input parts 2, the control unit 6, and the monitor 7 are disposed.

Figure 3:
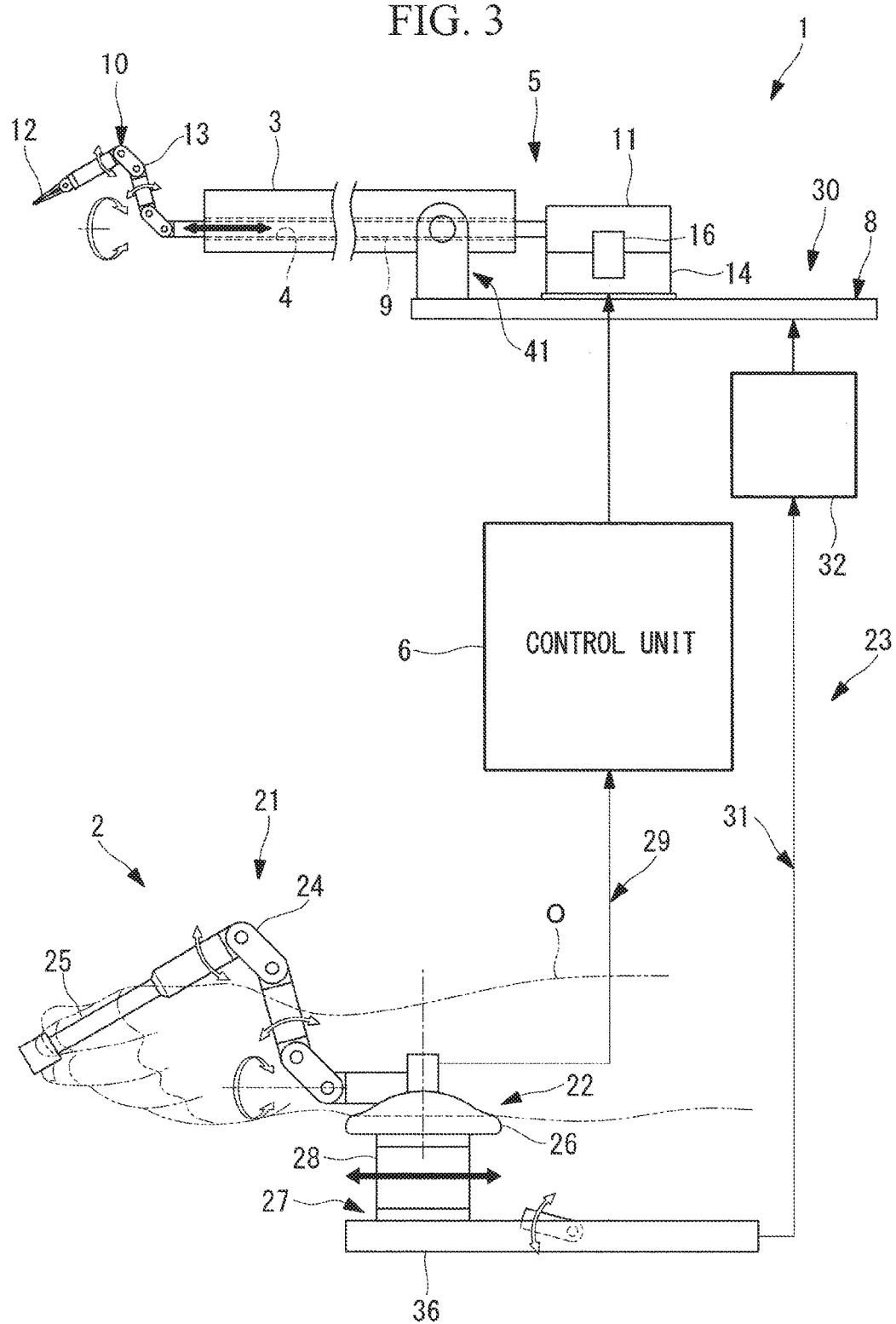
FIG. 3 shows a manipulator, an operation input part, and a control unit used in the medical manipulator system in FIG. 1.

As shown in FIG. 3, each manipulator 5 includes an insertion section (elongated member) 9 that is inserted into the body of the patient P via the channel 4 in the over tube 3 (described below), a movable part 10 provided at the distal end of the insertion section 9, and a proximal-end driving part 11 that is disposed at the proximal end side of the insertion section 9 and drives the movable part 10 with a power transmitting member, such as a wire (not shown).

The movable part 10 includes a treatment part 12 that is provided at the most distal end and that acts on and treats an affected part inside the body, and a plurality of joints 13 that change the position of the distal end and the posture of the treatment part 12. The treatment part 12 is, for example, grasping forceps or a high-frequency knife.

The proximal-end driving part 11 has an engaging part 16 that is detachably connected to an engaging recess 15 provided in a motor unit 14 (described below).

The over tube 3 is made of a flexible material and includes, as shown in FIG. 2, a distal-end-side tubular section 19 having the two manipulator channels (channels) 4 through which the manipulators 5 are individually inserted and a single endoscope channel 18 through which an endoscope 17 is inserted, and a proximal-end-side tubular section (proximal end part) 20 that extends from the proximal end of the distal-end-side tubular section 19 so as to extend the two manipulator channels 4 toward the proximal end side and splits into two portions at the proximal end side thereof.

As shown in FIG. 3, each operation input part 2 includes a first operating part 21 that is grasped in the hand of the operator O and is operated, a second operating part 22 that is operated with the wrist or arm of the operator O, and an instruction transmitting unit 23 that transmits operation instructions input by the operating parts 21 and 22 to the manipulator 5.

The first operating part 21 is configured to have a shape similar to the shape of the movable part 10 of the manipulator 5. A distal end part 25 that is supported by the same number of joints 24 as the joints of the movable part 10 is grasped in the hand of the operator O and is moved by the palm or the fingers. The first operating part 21 is provided with sensors (not shown) for detecting the angles of the joints 24 constituting the first operating part 21.

The sensors generate electrical signals corresponding to the angles of the joints 24. With this configuration, each first operating part 21 can be used to input an operation instruction with the palm or fingers of the operator O and generate an action instruction composed of the electrical signals.

The second operating part 22 includes an arm rest 26 that is fixed to a base of the first operating part 21 and a translation mechanism 27 that supports the arm rest 26 and the first operating part 21 such that they can be moved in an integral manner. The arm rest 26 is disposed at a position on which an arm part near the wrist of the hand grasping the distal end part 25 when the operator O grasps the distal end part 25 of the first operating part 21 exactly rests.

The translation mechanism 27 includes a slider 28 to which the arm rest 26 and the first operating part 21 are fixed, and a linear guide 36 that supports the slider 28 so as to be horizontally movable, as shown by filled arrows in FIGS. 3 and 4. By horizontally moving the slider 28 with the arm on the arm rest 26, the position of the first operating part 21 can be changed while the posture in which the first operating part 21 is grasped is maintained. With this configuration, the second operating parts 22 can be used to input operation instructions with the wrists or arms of the operator O and can generate action instructions by converting the forces input with the wrists or the arms into mechanical driving forces of the two sliders 28.

Each instruction transmitting unit 23 includes an electric-signal transmitting unit 29 that connects the first operating part 21 and the proximal-end driving part 11, and a mechanical-power transmitting unit 31 that connects the second operating part 22 and an advancing-and-retracting mechanism 30.

The electric-signal transmitting unit 29 transmits an action instruction composed of an electric signal generated by the first operating part 21 to the control unit 6 and supplies an instruction signal generated by the control unit 6 to a motor of the motor unit 14. The control unit 6 calculates the amounts of rotational movement and rotation speeds of the motors of the motor units 14 according to the action instructions generated by the first operating parts 21 and controls the motors.

As shown in FIG. 3, each mechanical-power transmitting unit 31 includes a transmitting unit 32 that converts a linear action for moving the slider 28 of the operation input part 2 forward and backward into a linear action of the advancing-and-retracting mechanism 30.

As shown in FIG. 4, each transmitting unit 32 includes a first rack-and-pinion mechanism 33 that converts the amount of linear movement of the slider 28 of the operation input part 2 into the rotation angle, a second rack-and-pinion mechanism 34 that converts the rotation action into the amount of linear movement of the advancing-and-retracting mechanism 30, pulleys 37 and 38 fixed to pinion gears 35 of the rack-and-pinion mechanisms 33 and 34, and a belt 39 stretched between the pulleys 37 and 38.

Note that components that electrically transmit power may be employed instead of the mechanical-power transmitting units 31.

Figure 5A:
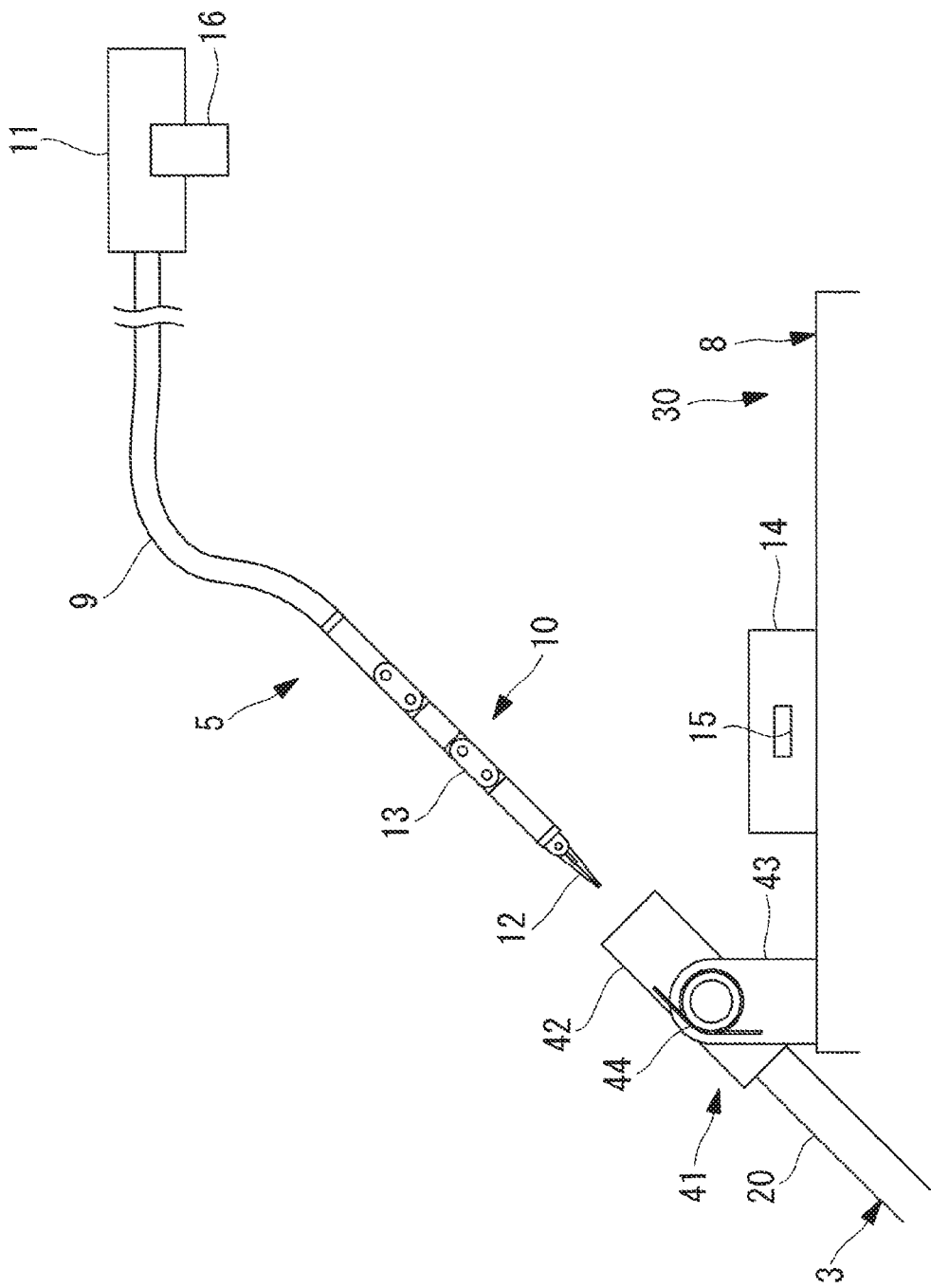
FIG. 5A is a front view showing a state before the manipulator is inserted into a manipulator channel from the proximal end of an over tube attached to a support part on the top surface of a console of the medical manipulator system in FIG. 1.
Figure 5B:
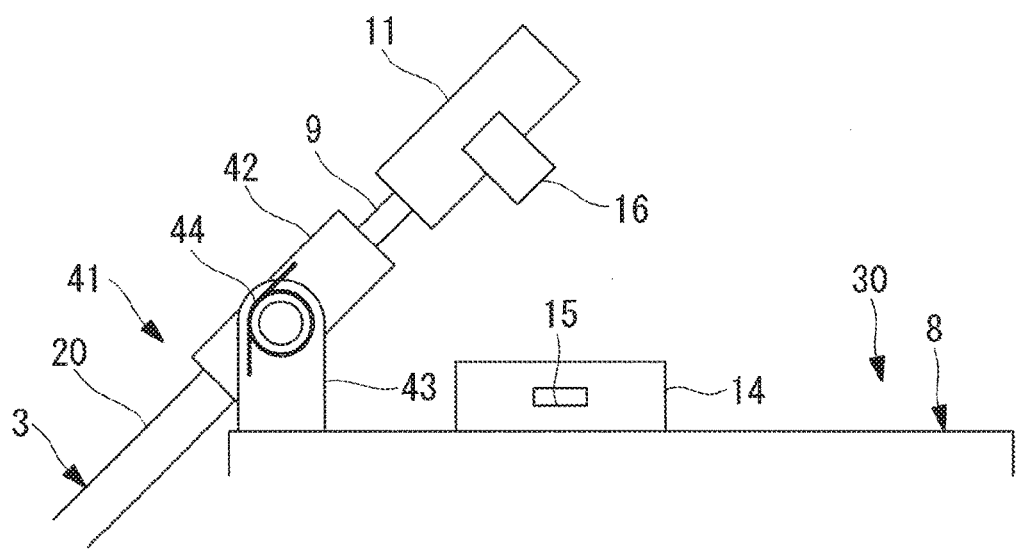
FIG. 5B is a front view showing a state in which, in the state in FIG. 5A, the manipulator is inserted, and the insertion is completed.
Figure 5C:
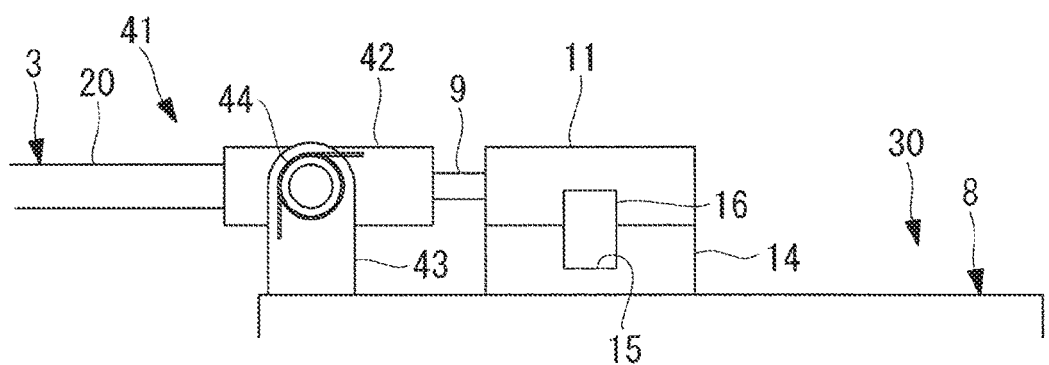
FIG. 5C is a front view showing a state in which, in the state in FIG. 5B, a movable part is pivoted, and a proximal-end driving part of the manipulator is connected to a motor unit.

As shown in FIGS. 5A to 5C, the console 8 is provided with, on the horizontally disposed flat top surface thereof: two support parts 41 to which the proximal end parts of the proximal-end-side tubular section 20 of the over tube 3 are attached; the motor units (driving sources) 14 to which the proximal-end driving parts 11 of the manipulators 5 inserted through the over tube 3 are detachably connected, each of the motor units 14 accommodating a motor (not shown) and the like for supplying power to the proximal-end driving parts 11; and the advancing-and-retracting mechanisms 30 that linearly move the motor units 14.

Each support part 41 includes a movable member (movable part) 42 to which the proximal end part of the proximal-end-side tubular section 20 of the over tube 3 is attached, a bracket 43 via which the movable member 42 is attached to the top surface of the console 8 so as to be pivotable about a horizontal axis, and a spring (urging part, springy member) 44 that urges the proximal end side of the movable member 42 upward. The spring 44 is, for example, a torsion spring disposed between the bracket 43 and the movable member 42 but is not limited thereto.

Specifically, the movable member 42 of each support part 41 can move the opening of the channel 4, which is provided at an end surface of the proximal-end-side tubular section 20 and into which the manipulator 5 is inserted, between a position (first position) where the opening is oriented in the horizontal direction and a position (second position) where the opening is oriented obliquely upward, by pivoting the proximal-end-side tubular section 20 of the over tube 3 attached to the movable member 42 about the horizontal axis. In a state in which the manipulator 5 is not inserted, and in a state in which the proximal-end driving part 11 of the manipulator 5 is not connected to the motor unit 14 on the top surface of the console 8, the movable member 42 is urged by the spring 44 such that the opening of the proximal-end-side tubular section 20 of the over tube 3 is oriented obliquely upward.

The operation of the thus-configured medical manipulator system 1 according to this embodiment will be described below.

When an affected part in the body of a patient P is treated with the medical manipulator system 1 according to this embodiment, the over tube 3 is inserted into the body cavity of the patient P, and the proximal-end-side tubular section 20 of the over tube 3 is attached to the movable members 42 of the support parts 41 provided on the top surface of the console 8. Furthermore, an insertion section of the endoscope 17 is inserted through the endoscope channel 18 in the over tube 3.

In this state, as shown in FIG. 5A, the openings of the proximal-end-side tubular section 20 of the over tube 3 are urged obliquely upward by the springs 44 provided on the support parts 41. Thus, the working efficiency in inserting the manipulators 5 into the manipulator channels 4 in the over tube 3 from the openings can be improved.

Specifically, because the openings of the proximal-end-side tubular section 20 of the over tube 3 are oriented obliquely upward, the manipulators 5 can be inserted from obliquely above, and thus, the manipulators 5 can be handled at a position sufficiently away from the top surface of the console 8.

Because the motor units 14, which are difficult to sterilize, are disposed on the top surface of the console 8, by handling the manipulators 5 at a position sufficiently away from the top surface of the console 8, the risk of the manipulators 5 touching the motor units 14 can be reduced, and thus, the cleanliness of the manipulators 5 can be maintained. Hence, the operator O who inserts the manipulators 5 into the over tube 3 can pay less attention when he/she operates the manipulators 5 so as not to touch the top surface of the console 8, leading to an advantage that the working efficiency can be improved.

As shown in FIG. 5B, after the manipulators 5 have been sufficiently inserted into the manipulator channels 4, as shown in FIG. 5C, the movable members 42 are pivoted against the urging force of the springs 44 to positions where the movable members 42 are substantially horizontal, and the proximal-end driving parts 11 of the manipulators 5 are connected to the motor units 14 on the top surface of the console 8.

By engaging the engaging parts 16 provided on the proximal-end driving parts 11 of the manipulators 5 with the engaging recesses 15 provided in the motor units 14, the proximal-end driving parts 11 and the motor units 14 are maintained connected. As a result, the driving force of the motor units 14 can be transmitted to the proximal-end driving parts 11.

Once the proximal-end driving parts 11 are connected to the motor units 14, the manipulators 5 are in contact with the motor units 14, which are difficult to sterilize. Thus, the cleanliness of the proximal-end driving parts 11 of the manipulators 5 is lost. However, the cleanliness of the movable parts 10 at the distal ends of the manipulators 5, which are disposed in the body of the patient P, is not lost because the long elongated member 9 is provided between the proximal-end driving parts 11 and the movable parts 10.

In this state, as shown in FIG. 3, the distal ends of the manipulators 5 project from the distal ends of the manipulator channels 4 in the over tube 3 and are disposed near the affected part in the body cavity, and the operator O operates the operation input parts 2 while viewing, on the monitors 7, the images acquired by the endoscope 17. When operating the operation input parts 2, as shown in FIG. 4, the operator O grasps the distal end parts 25 of the pair of first operating parts 21 in both hands and rests both arms on the arm rests 26 of the pair of second operating parts 22.

When the operator O applies a force to one of the arm rests 26 from one arm, the slider 28 to which the arm rest 26 is fixed moves in the direction of that force, and the amount of linear movement is converted into the rotation angle by the first rack-and-pinion mechanism 33.

The amount of linear movement converted into the rotation angle of the first rack-and-pinion mechanism 33 is transmitted to the second rack-and-pinion mechanism 34 via the pulleys 37 and 38 and the belt 39 and is converted into the amount of linear movement of the advancing-and-retracting mechanism 30. Because the motor unit 14 is fixed to the advancing-and-retracting mechanism 30, the proximal-end driving part 11, the elongated member 9, and the movable part 10 connected to the motor units 14 are integrally moved in the longitudinal direction of the elongated member 9. As a result, the treatment part 12 located at the distal end of the movable part 10 is roughly moved in the front-rear direction.

When the operator O moves the distal end parts 25 of the first operating parts 21 that he/she grasps in both hands with the force of the palms or fingers, the amounts of movement are detected by the sensors provided on the joints 24 and are transmitted to the control unit 6 in the form of electric signals. The control unit 6 calculates electric action instructions for moving the joints 13 of the movable parts 10 such that their angles are equal to the angles of the joints 24 detected by the sensors and supplies the instructions to the motors of the motor units 14 connected to the joints 13. As a result, the distal end portions of the treatment parts 12 provided at the distal ends of the movable parts 10 are precisely moved by electric power, according to the instructions given by the palms or fingers.

When the manipulators 5 are pulled out of the over tube 3 after the affected part in the body has been treated in this way, the engaging parts 16 provided on the proximal-end driving parts 11 of the manipulators 5 and the engaging recesses 15 in the motor units 14 are disengaged, and the proximal-end driving parts 11 are detached from the motor units 14. As a result, the movable members 42 are pivoted by the springs 44, and the openings of the proximal-end-side tubular section 20 of the over tube 3 are oriented obliquely upward. Thus, the manipulators 5 can be pulled out in the obliquely upward direction.

Also in this case, according to this embodiment, the manipulators 5 can be pulled out at a position away from the top surface of the console 8. Accordingly, the risk of the distal end parts of the manipulators 5 disposed in the body of the patient P touching the console 8 can be reduced.

Furthermore, when the manipulators 5 are pulled out of the over tube 3, body fluid, such as blood, of the patient P may flow out of the body through the manipulator channels 4 in the over tube 3. Also in this case, by orienting the openings of the proximal-end-side tubular section 20 of the over tube 3 obliquely upward to increase the hydraulic head, the body fluid can be prevented from flowing out of the openings.

In this embodiment, the movable members 42 to which the proximal-end-side tubular section 20 of the over tube 3 is attached are pivoted about the horizontal axis to move the openings provided at the proximal end parts away from the top surface of the console 8. Alternately, the movable members 42 may be moved in the up-and-down direction keeping the posture of each movable member 42.

Furthermore, although the movable members 42 are pivoted by the springs 44, the movable members 42 may be driven by motors or the like.

Figure 6A:
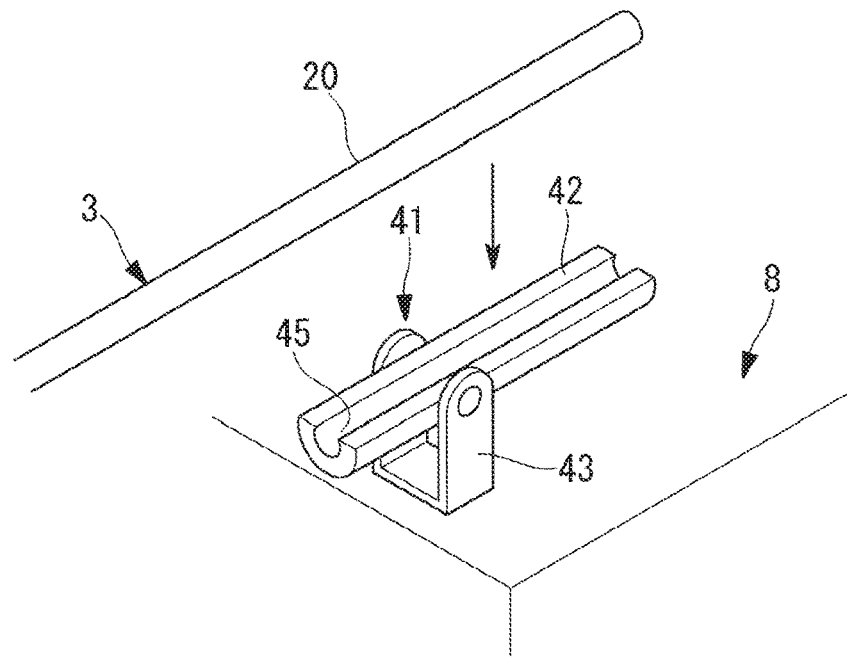
FIG. 6A is a perspective view showing a modification of the support part in the medical manipulator system in FIG. 1.
Figure 6B:
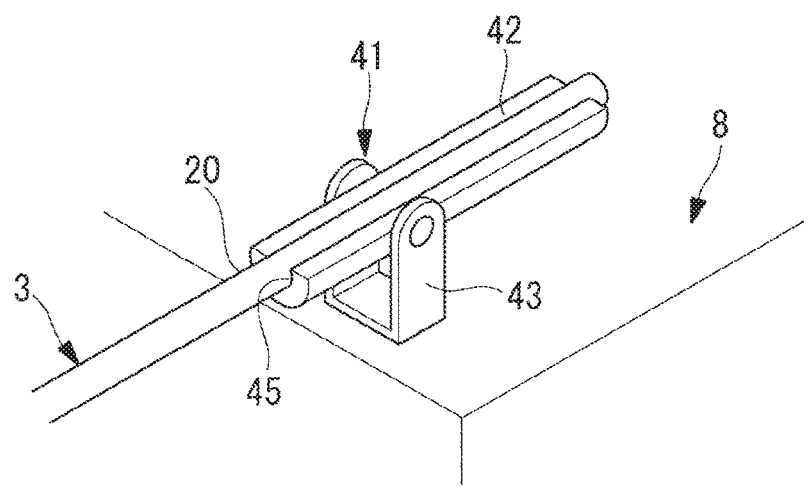
FIG. 6B is a perspective view showing a state in which the over tube is fitted and attached to a groove provided in the movable part of the support part in FIG. 6A.

Furthermore, in this embodiment, as shown in FIGS. 6A and 6B, the movable members 42 of the support parts 41 may be configured to detachably receive the proximal-end-side tubular section 20 of the over tube 3. For example, in the example shown in FIGS. 6A and 6B, movable members 42 having grooves 45 that become narrower toward their openings, in cross section, may be employed.

With this configuration, the over tube 3 can be easily attached to the movable members 42 by fitting the over tube 3 to the openings of the grooves 45 and pressing the over tube 3 into the grooves 45 while elastically deforming the over tube 3 or elastically deforming the support parts 41. When the support parts 41 are elastically deformed, the elastically deformed support parts 41 themselves serve as the above-described torsion springs, and, in this case, the torsion springs can be omitted.

Figure 7A:
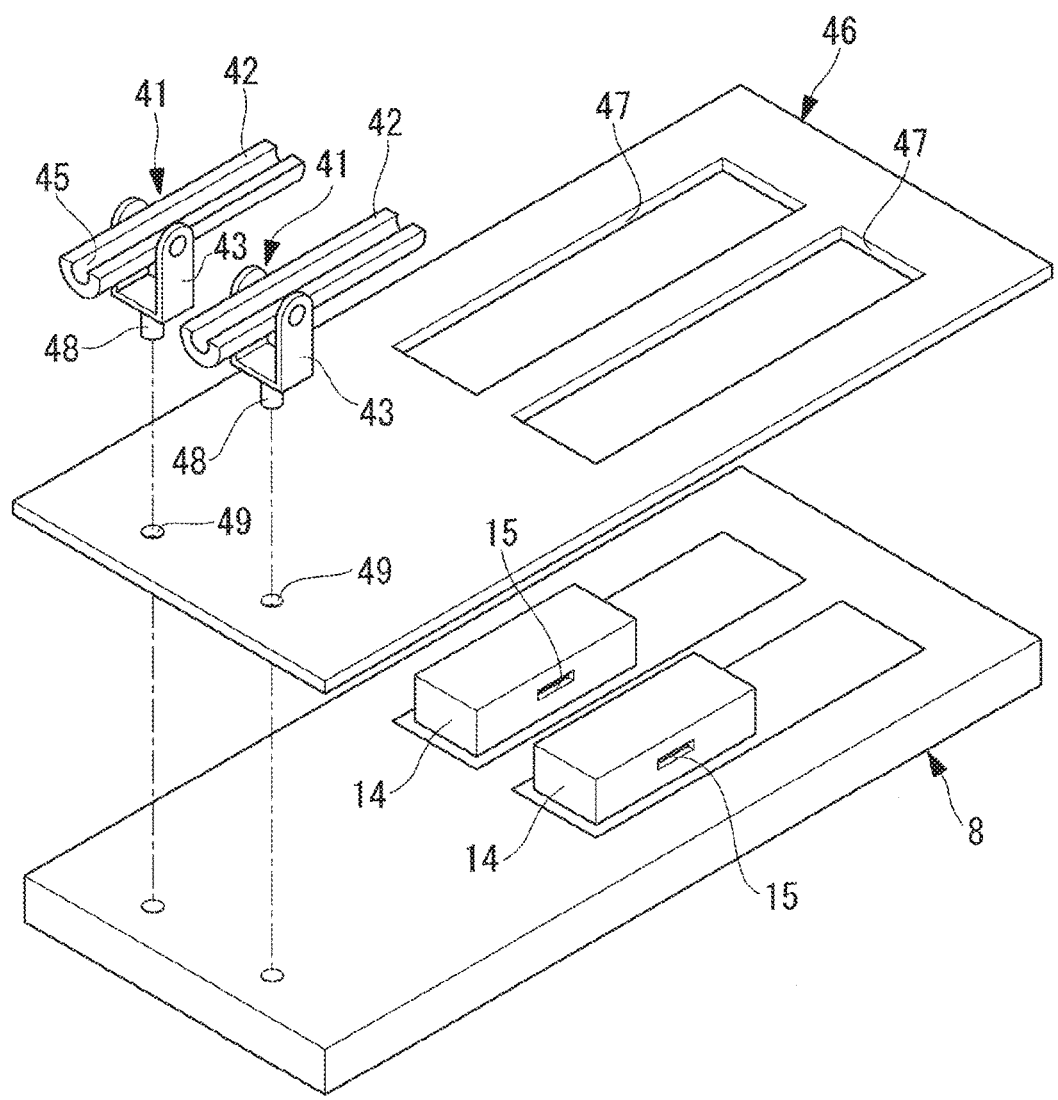
FIG. 7A is an exploded perspective view of a modification of the medical manipulator system in FIG. 1, showing a case where a drape is provided.
Figure 7B:
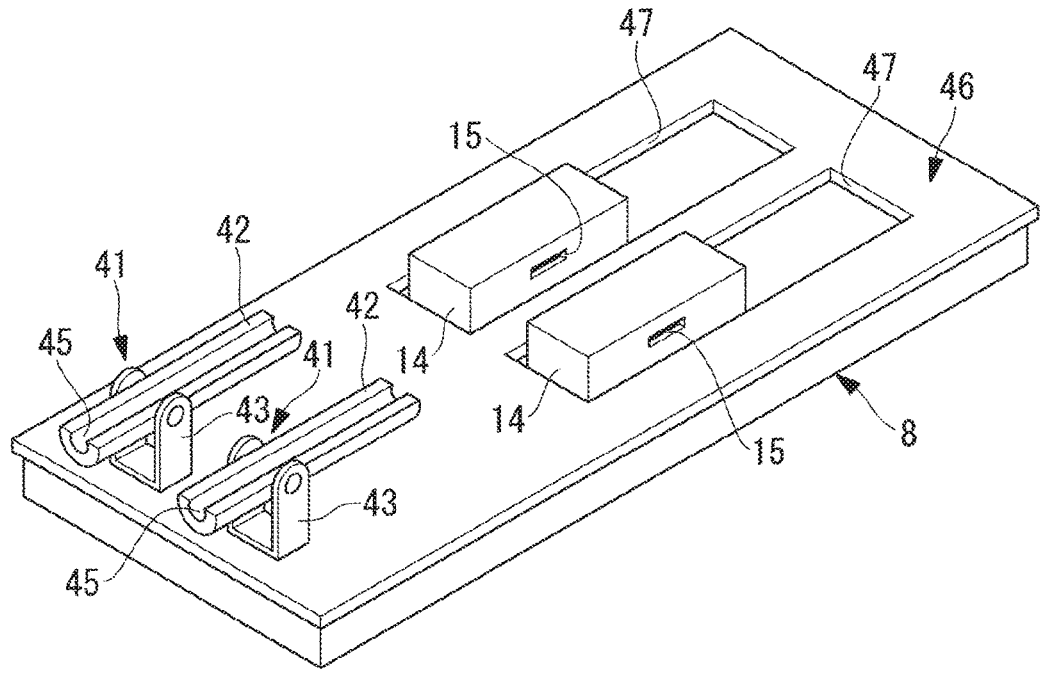
FIG. 7B is a perspective view showing a state in which the console, the drape, and the support part in FIG. 7A are assembled.

Furthermore, in this embodiment, as shown in FIGS. 7A and 7B, the brackets 43 of the support parts 41 may be configured to be attachable to and detachable from the top surface of the console 8, and the brackets 43 of the support parts 41 may be attached to the console 8 with the top surface of the console 8 being covered by a drape 46.

The drape 46 is provided with openings 47 through which the motor units 14, which are linearly moved by the advancing-and-retracting mechanisms 30, are exposed at the upper side and holes 49 through which shafts 48 for attaching the brackets 43 of the support parts 41 to the top surface of the console 8 extend.

The drape 46 may be made of a relatively hard material that is less likely to be deformed, such as silicone rubber or plastic.

By employing the drape 46 for covering the top surface of the console 8, the chances of the manipulators 5 touching a dirty area of the top surface of the console 8 when the manipulators 5 are inserted into the manipulator channels 4 in the over tube 3 can be further reduced, leading to an advantage that the cleanliness can be maintained.

Furthermore, the support parts 41 and the drape 46 may be integrally formed.

Moreover, the proximal-end-side tubular section 20 of the over tube 3 and the movable members 42 may be undetachably provided, and the brackets 43 may be detachably provided on the top surface of the console 8.

Furthermore, it is also possible to employ a configuration in which the proximal-end-side tubular section 20 of the over tube 3 and the movable members 42 are undetachably provided, the brackets 43 and the drape 46 are undetachably provided, and the brackets 43 are detachably attached to the console 8 when the top surface of the console 8 is covered by the drape 46.

Furthermore, it is also possible that a deformable soft material, such as a thin vinyl sheet, is used for the drape 46, and the proximal-end-side tubular section 20 of the over tube 3 is fitted into the grooves 45 provided in the movable members 42, which have the shape as shown in FIG. 6A, with the drape 46 therebetween. In this case, the support parts 41 may be undetachably fixed to the top surface of the console 8.

Figure 8:
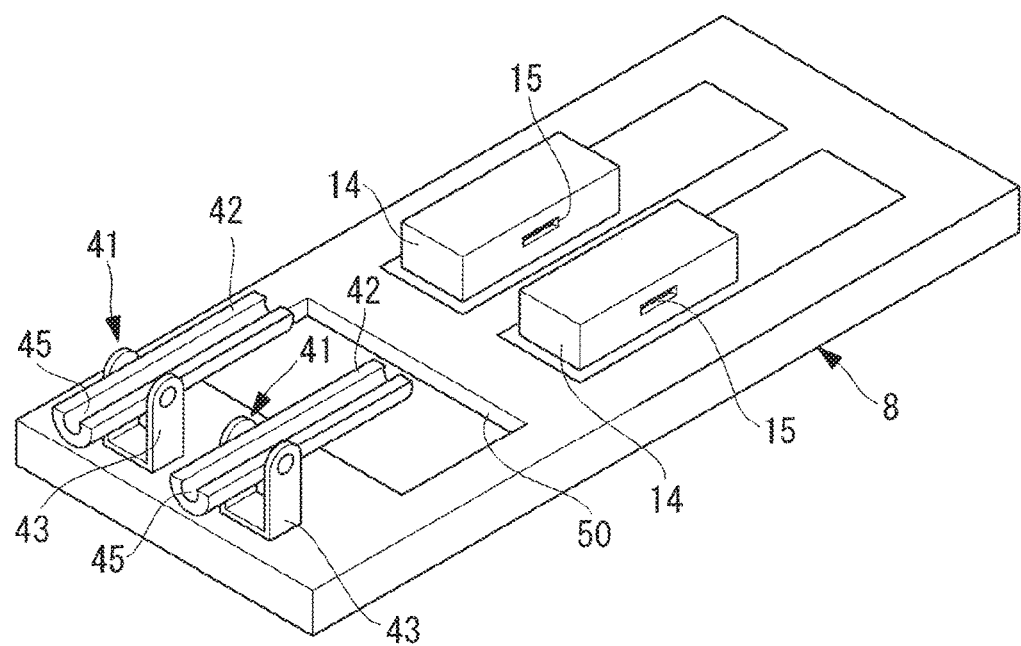
FIG. 8 is a perspective view of the console in another modification of the medical manipulator system in FIG. 1.

Furthermore, as shown in FIG. 8, a recess 50 may be provided in the top surface of the console 8, at a position vertically below the proximal end side of the movable members 42 of the support parts 41. With this configuration, when the manipulators 5 are pulled out of the manipulator channels 4, the body fluid, such as blood, flowing from the body of the patient P through the manipulator channels 4 can be accumulated and prevented from flowing outside.

Furthermore, in this embodiment, although the support parts 41 provided on the console 8 have been shown as an example, instead, the support parts 41 provided on the proximal-end-side tubular section 20 of the over tube 3 may be employed.

This configuration makes cleaning and sterilization of the support parts 41 easy. More specifically, because the operator O does not need to consider the cleanliness of the support parts 41 during treatment, treatment can be more easily performed.

The inventors have arrived at the following aspects of the present invention.

An aspect of the present invention is a medical manipulator system including: a manipulator having a treatment part at a distal end of an elongated member and having a proximal-end driving part for driving the treatment part at a proximal end of the elongated member; an over tube having a channel through which the manipulator passes in a longitudinal direction of the over tube; and a base provided with, on a top surface thereof, a support part to which a proximal end part of the over tube is attached, and a driving source that is detachably connected to the proximal-end driving part of the manipulator inserted into the channel from the proximal end part of the over tube to supply a driving force to the proximal-end driving part, wherein the support part includes: a movable part provided so as to be movable between a first position where a longitudinal axis of the proximal end part of the over tube attached to the movable part is supported horizontally and a second position where the proximal end is supported at a position farther from the top surface than at the first position; and an urging part that moves the movable part to the second position during the proximal-end driving part is not connected to the driving source.

According to this aspect, with the proximal end part of the over tube, which is inserted into the body of the patient, being attached to the movable part of the support part, by inserting the elongated member of the manipulator into the channel in the over tube from the treatment part side at the distal end so as to penetrate therethrough, allowing the treatment part to project from the distal end of the over tube, and by connecting the proximal-end driving part exposed from the proximal end of the over tube to the driving source on the base, it is possible to operate the proximal-end driving part with the driving force from the driving source and to treat the affected part by driving the treatment part with the proximal-end driving part.

In this case, when the manipulator is inserted into the channel in the over tube, the movable part of the support part is located at the second position by the function of the urging part. Because the proximal end part of the over tube is farther from the top surface of the base in the second position than in the first position, insertion can be performed without worrying that the manipulator touches the top surface of the base. Thus, the ease of insertion can be improved.

After insertion is completed, by moving the movable part from the second position to the first position, the longitudinal axis of the proximal end part of the over tube is made horizontal, thus making the manipulator projecting from the proximal end part horizontal. By doing so, the proximal-end driving part of the manipulator can be easily attached to the driving source provided on the top surface of the base.

In the above aspect, the movable part may be provided so as to be pivotable about a horizontal axis.

With this configuration, when the movable part is pivoted about the horizontal axis and is disposed at the first position, the longitudinal axis at the proximal end part of the over tube attached to the movable part is disposed horizontally, and thus, connection between the proximal-end driving part of the manipulator and the driving source can be made easy.

On the other hand, in a state in which the proximal-end driving part of the manipulator is not connected to the driving source, the movable part is pivoted about the horizontal axis by the urging part and is disposed at the second position. Thus, the opening of the channel provided at the proximal end part is oriented upward or obliquely upward. Hence, when the manipulator is inserted, the proximal end part is away from the top surface of the base. Thus, insertion can be performed from above or obliquely above without worrying that the manipulator touches the top surface of the base. Thus, the ease of insertion can be improved.

Furthermore, when the manipulator is detached from the over tube, body fluid, such as blood, may flow out of the body of the patient through the channel in the over tube. However, by orienting the opening of the channel upward or obliquely upward, the body fluid can be made less likely to flow out from the opening.

Furthermore, in the above aspect, the urging part may be a springy member that gives the support part a springy force toward the second position.

With this configuration, when the manipulator is inserted, the movable part of the support part is moved to the second position by the springy force of the springy member, improving the ease of insertion, and, when the proximal-end driving part is to be connected to the driving source, the connection can be easily performed by moving the movable part of the support part to the first position against the springy force of the springy member.

Furthermore, in the above aspect, the support part may be detachably provided on the base, the medical manipulator system may further comprise a drape that covers at least a portion of the base, and the support part may be attached to the base so that the drape is sandwiched therebetween.

With this configuration, when the drape is attached to the base, at least a portion of the base is covered by the drape. The support part can be attached to the base with the drape therebetween, the manipulator can be inserted into the channel from the proximal end part of the over tube attached to the movable part of the support part that is disposed on the drape and is located at the second position, the movable part can be positioned at the first position, and the proximal-end driving part of the manipulator can be connected to the driving source. By covering the base with the drape, chances of the manipulator touching a dirty part can be reduced.

Furthermore, in the above aspect, the support part may be detachably provided on the base and include, as an integral part, a drape that is fitted to the base so as to cover at least a portion of the base.

With this configuration, when the support part is attached to the base, the drape provided as an integral part of the support part is attached so as to cover at least a portion of the base.

Furthermore, in the above aspect, the over tube may be detachably attached to the movable part of the support part, the medical manipulator system may further comprise a drape that covers at least a portion of the base, and the over tube may be attached to the movable part so that the drape is sandwiched therebetween.

With this configuration, by placing, from above, the drape on the support part that is attached to at least a portion of the base, the drape covers at least a portion of the base including the support part. In this state, by attaching the proximal end part of the over tube to the movable part of the support part with the drape therebetween, the over tube and the manipulator alone can be exposed to the outside of the drape.

Furthermore, in the above aspect, the drape may have an opening through which at least the driving source is exposed, and may cover the base so that the driving source is exposed from the opening.

With this configuration, when the drape is attached to the base, the base is covered by the drape with the driving part being exposed from the opening provided in the drape. The proximal-end driving part of the manipulator can be connected to the driving source exposed from the opening provided in the drape.

Furthermore, in the above aspect, the base may have a recess capable of accumulating liquid at a position vertically below the proximal end part of the over tube attached to the movable part.

With this configuration, even if liquid flows out of the body of the patient through the channel when the manipulator is pulled out of the channel in the over tube, by receiving and accumulating the liquid in the recess provided at a position vertically below the proximal end part, the liquid can be prevented from flowing outside.

The aforementioned aspects provide an advantage in that it is possible to improve the ease of inserting a manipulator into a channel from the proximal end of an over tube that is fixed to a flat base.

REFERENCE SIGNS LIST 1 medical manipulator system
3 over tube
4 channel (manipulator channel)
5 manipulator
8 console (base)
9 insertion section (elongated member)
11 proximal-end driving part
12 treatment part
14 motor unit (driving source)
20 proximal-end-side tubular section (proximal end part)
41 support part
42 movable member (movable part)
44 spring (urging part, springy member)
46 drape
50 recess

The invention claimed is:

1. A medical manipulator system comprising:
   a manipulator having a insertion section extending in a longitudinal direction, the manipulator comprising:
      a treatment part provided at a distal end of the manipulator to perform treatment in a body;
      a proximal-end driving part provided at a proximal end of the manipulator, configured to drive the treatment part,
   an over tube having a channel through which the manipulator passes, the channel extending along a longitudinal direction of the over tube; and
   a base to which the over tube is attached,
   wherein the base comprises:
      a support part which supports a proximal end portion of the over tube; and
      a driving source configured to detachably connect with the proximal-end driving part, the driving source configured to supply a driving force to the proximal-end driving part when the proximal-end driving part is attached to the driving source,
   wherein the support part comprises:
      a movable part configured to move the proximal end portion of the over tube, which is supported by the support part, between a first position and a second position in a state in which the manipulator is inserted into the channel of the over tube, the first position being a position where the proximal-end driving part is connected to the driving source, the second position being a position where the proximal-end driving part is disconnected from the driving source;
   an urging part that is configured to move the movable part to the second position in a state in which the proximal-end driving part is not connected to the driving source.

2. The medical manipulator system according to claim 1, wherein the movable part is provided so as to be pivotable about a horizontal axis.

3. The medical manipulator system according to claim 1, wherein the urging part is a springy member that gives the support part a springy force toward the second position.

4. The medical manipulator system according to claim 1, wherein
the support part is detachably provided on the base,
the medical manipulator system further comprises a drape that covers at least a portion of the base, and
the support part is attached to the base so that the drape is sandwiched therebetween.

5. The medical manipulator system according to claim 4, wherein the drape has an opening through which at least the driving source is exposed, and covers the base so that the driving source is exposed from the opening.

6. The medical manipulator system according to claim 1, wherein the support part is detachably provided on the base and includes, as an integral part, a drape that is fitted to the base so as to cover at least a portion of the base.

7. The medical manipulator system according to claim 1, wherein
the over tube is detachably attached to the movable part of the support part,
the medical manipulator system further comprises a drape that covers at least a portion of the base, and
the over tube is attached to the movable part so that the drape is sandwiched therebetween.

8. The medical manipulator system according to claim 1, wherein the base has a recess capable of accumulating liquid at a position vertically below the proximal end part of the over tube attached to the movable part.

9. The medical manipulator system according to claim 1, wherein the support part comprises a bracket attached to a top surface of the base, and
wherein the urging part comprises a torsion spring for pivoting a distal end and a proximal end of the movable part around a horizontal axis.

10. A medical support device to which a manipulator having a treatment part at its distal end section and having a proximal-end driving part for driving the treatment part at its proximal end section is connected, the medical support device comprising:
an over tube having a channel through which the manipulator passes in a longitudinal direction of the over tube; and
a base to which the over tube is attached,
wherein the base comprises:
a support part which supports a proximal end portion of the over tube; and
a driving source configured to detachably connect with the proximal-end driving part, the driving source configured to supply a driving force to the proximal-end driving part when the proximal-end driving part is attached to the driving source,
wherein the support part comprises:
a movable part configured to move the proximal end portion of the over tube, which is supported by the support part, between a first position and a second position in a state in which the manipulator is inserted into the channel of the over tube, the first position being a position where the proximal-end driving part is connected to the driving source, the second position being a position where the proximal-end driving part is disconnected from the driving source; and
an urging part that moves the movable part to the second position in a state in which the proximal-end driving part is not connected to the driving source.

11. The medical support device according to claim 10, wherein the movable part is provided so as to be pivotable about a horizontal axis.

12. The medical support device according to claim 10, wherein the urging part is a springy member that gives the support part a springy force toward the second position.

13. The medical support device according to claim 10, wherein
the support part is detachably provided on the base,
the medical manipulator system further comprises a drape that covers at least a portion of the base, and
the support part is attached to the base so that the drape is sandwiched therebetween.

14. The medical support device according to claim 10, wherein the support part is detachably provided on the base and includes, as an integral part, a drape that is fitted to the base so as to cover at least a portion of the base.

15. The medical support device according to claim 14, wherein the drape has an opening through which at least the driving source is exposed, and covers the base so that the driving source is exposed from the opening.

16. The medical support device according to claim 10, wherein
the over tube is detachably attached to the movable part of the support part,
the medical manipulator system further comprises a drape that covers at least a portion of the base, and
the over tube is attached to the movable part so that the drape is sandwiched therebetween.

17. The medical support device according to claim 10, wherein the base has a recess configured to accumulate liquid at a position vertically below the proximal end part of the over tube attached to the movable part.

* * * * *